(12) United States Patent
Kim et al.

(10) Patent No.: US 9,557,316 B2
(45) Date of Patent: Jan. 31, 2017

(54) SAMPLE ANALYSIS METHODS AND APPARATUSES AND DYNAMIC VALVE OPERATION METHODS

(71) Applicant: Samsung Electronics Co., Ltd., Suwon-si, Gyeonggi-do (KR)

(72) Inventors: Minseok S. Kim, Yongin-si (KR); Hui-sung Moon, Yongin-si (KR); Jong-myeon Park, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/261,708

(22) Filed: Apr. 25, 2014

(65) Prior Publication Data

US 2015/0104814 A1 Apr. 16, 2015

(30) Foreign Application Priority Data

Oct. 15, 2013 (KR) .......................... 10-2013-0122961

(51) Int. Cl.
*B01L 3/00* (2006.01)
*G01N 21/00* (2006.01)
(Continued)

(52) U.S. Cl.
CPC ....... *G01N 33/491* (2013.01); *B01L 3/502738* (2013.01); *B01L 3/50273* (2013.01); *B01L 3/502715* (2013.01); *B01L 3/502753* (2013.01); *B01L 2200/0652* (2013.01); *B01L 2200/10* (2013.01); *B01L 2200/14* (2013.01); *B01L 2300/0803* (2013.01); *B01L 2300/0864* (2013.01); *B01L 2300/1861* (2013.01); *B01L 2400/0409* (2013.01);
(Continued)

(58) Field of Classification Search
CPC ................ B01L 2200/0652; B01L 2300/0803; B01L 2300/0864; B01L 2300/1861; B01L 2400/0409; B01L 2400/0677; B01L 3/502738; B01L 3/502753; G01N 33/491
See application file for complete search history.

(56) References Cited

U.S. PATENT DOCUMENTS 6,833,536 B2 12/2004 Shigeura
7,068,874 B2 6/2006 Wang et al.
(Continued)

FOREIGN PATENT DOCUMENTS

KR 10-0744556 A 6/2007

*Primary Examiner* — Jennifer Wecker
(74) *Attorney, Agent, or Firm* — Leydig, Voit & Mayer, Ltd.

(57) ABSTRACT

Disclosed are sample analysis apparatus and methods. A sample analysis apparatus includes a first unit that rotates a microfluidic apparatus including: a chamber having a space accommodating a sample, a channel that provides a path through which the sample flows; and a valve that selectively opens and closes the channel, a valve driver that supplies energy, used to operate the valve, to the valve in a state of being separated from the microfluidic apparatus, a third unit that rotates the valve driver with respect to a common rotation axis with a rotation axis of the microfluidic apparatus and the third unit, and a control unit that controls the first and third units and the valve driver to supply energy to the valve while the microfluidic apparatus and the valve driver are being rotated at the same rotation speed.

9 Claims, 6 Drawing Sheets

(51) Int. Cl.
  *G05B 15/00* (2006.01)
  *G01N 33/49* (2006.01)
  *G01N 33/574* (2006.01)
  *F16K 99/00* (2006.01)

(52) U.S. Cl.
  CPC ... *B01L 2400/0677* (2013.01); *F16K 99/0001* (2013.01); *F16K 2099/0084* (2013.01); *Y10T 436/25375* (2015.01)

(56) References Cited

U.S. PATENT DOCUMENTS

| | | | |
|---|---|---|---|
| 7,355,716 B2 * | 4/2008 | de Boer | A61B 5/0059 356/479 |
| 7,980,272 B2 | 7/2011 | Park et al. | |
| 7,998,433 B2 | 8/2011 | Park et al. | |
| 8,191,715 B2 | 6/2012 | Cho et al. | |
| 8,221,704 B2 | 7/2012 | Park et al. | |
| 2007/0009382 A1 | 1/2007 | Bedingham et al. | |
| 2007/0009383 A1 * | 1/2007 | Bedingham | B01L 3/502715 422/63 |
| 2008/0058192 A1 * | 3/2008 | Cho | B01L 3/502738 494/1 |
| 2008/0058991 A1 * | 3/2008 | Lee | B01L 3/5027 700/266 |
| 2008/0193336 A1 * | 8/2008 | Cho | B01L 3/50273 422/400 |
| 2008/0226504 A1 | 9/2008 | Park et al. | |
| 2008/0269077 A1 * | 10/2008 | Lee | B01L 3/50273 506/33 |
| 2009/0282681 A1 | 11/2009 | Park et al. | |
| 2009/0326827 A1 * | 12/2009 | Mostowfi | B01L 3/502784 702/12 |
| 2011/0014094 A1 * | 1/2011 | Kim | B01L 3/5027 422/400 |
| 2011/0194114 A1 * | 8/2011 | Yeo | B01L 3/5027 356/435 |
| 2011/0256026 A1 * | 10/2011 | Kim | B01L 3/50273 422/82.05 |
| 2012/0122160 A1 * | 5/2012 | Saito | B01L 7/525 435/91.2 |
| 2012/0293796 A1 * | 11/2012 | Ludowise | B01L 3/5027 356/244 |

\* cited by examiner

SAMPLE ANALYSIS METHODS AND APPARATUSES AND DYNAMIC VALVE OPERATION METHODS

RELATED APPLICATIONS

This application claims the benefit of Korean Patent Application No. 10-2013-0122961, filed on Oct. 15, 2013, in the Korean Intellectual Property Office, the disclosure of which is incorporated herein in its entirety by reference.

BACKGROUND

1. Field

The present disclosure relates to sample analysis methods and apparatuses that analyze a sample by using a microfluidic apparatus including a valve operated with external energy, and to methods of dynamically opening and closing a valve.

2. Description of the Related Art

Most deaths relating to malignant tumors are caused by metastasis of the tumor from an initial position where a tumor occurs, to a tissue and an organ which are separated from the initial position. Therefore, early detection of tumor metastasis is an important factor for increasing a survival probability of a cancer patient, and early tumor detection and monitoring of tumor growth are considered very important factors in successfully treating a cancer patient. It is known that circulating tumor cells (CTCs) are detected from a patient before a tumor is detected for the first time. Therefore, CTCs play an important role in early detection and prediction of cancer. Also, since cancer is generally metastasized through blood, a CTC may be an indicator for diagnosing whether cancer is metastasized.

Sample analysis, which typically involves separating a target cell such as a CTC, a cancer cell, or a cancer stem cell from a sample, may use a disk-shaped microfluidic apparatus including a microfluidic structure which causes a flow of a sample due to a centrifugal force. The microfluidic apparatus includes a valve used to control a flow of a sample. The valve operates with energy supplied from the an external source. In order to operate the valve, a sample analysis process stops rotation of the microfluidic apparatus, supplies energy to the valve to melt a valve material, and again rotates the microfluidic apparatus. However, samples centrifuged from a plurality of layers are again mixed in a process of operating the valve, causing degradation in the reliability of analysis. Also, the melted valve material is solidified in a process of again rotating the microfluidic apparatus, and thus the valve cannot operate or operates unstably.

SUMMARY

Provided are sample analysis methods and apparatuses for quickly and reliably operating a valve of a microfluidic apparatus, and dynamic valve operation methods.

Additional aspects will be set forth in part in the description which follows and, in part, will be apparent from the description, or may be learned by practice of the presented embodiments.

According to an aspect of the present invention, a sample analysis apparatus includes: a first unit that rotates a microfluidic apparatus including a chamber having a space for accommodating a sample; a channel that provides a path through which the sample flows; and a valve that selectively opens and closes the channel; a valve driver that supplies energy, used to operate the valve, to the valve in a state of being separated from the microfluidic apparatus; a third unit that rotates the valve driver with respect to a common rotation axis with a rotation axis of the microfluidic apparatus and the third unit; and a control unit that controls the first and third units and the valve driver to supply energy to the valve while the microfluidic apparatus and the valve driver are being rotated at the same rotation speed.

The sample analysis apparatus may further include a second unit that moves the valve driver in a radial direction of the microfluidic apparatus, wherein the control unit controls the first, second, and third units so that positions in the radial direction, and angular positions of the valve driver and the valve are aligned with each other.

The third unit may include: a rotary member that is provided to be rotatable with respect to the common rotation axis; and a motor that rotates the rotary member. The valve driver may be provided at the rotary member to be movable in the radial direction.

The sample analysis apparatus may further include a position detector that detects a reference position of the valve driver in the radial direction.

The sample analysis apparatus may further include: a first phase detector that detects a first phase pattern provided at the microfluidic apparatus; and a second phase detector that detects a second phase pattern provided at the valve driver, wherein the control unit may control angular positions of the valve and the valve driver, based on output signals of the first and second phase detectors.

While a sample processing process is being performed, the control unit may control the first unit to rotate the first flow apparatus at a first rotation speed, and while the valve is operating, the control unit may control the first and third units to rotate the microfluidic apparatus and the valve driver at a second rotation speed.

The first rotation speed may be the same as the second rotation speed.

The first rotation speed may differ from the second rotation speed.

The second rotation speed may be lower than the first rotation speed.

The valve may include a valve material that is melted by energy supplied from the valve driver.

The valve material may be melted, and the melted valve material may be discharged or moved through the channel by centrifugal force, generated by the rotation of the microfluidic apparatus, to open or close the channel.

According to another aspect of the present invention, a sample analysis method includes: rotating a microfluidic apparatus at a first rotation speed to perform sample processing, the microfluidic apparatus including: a chamber that is a space accommodating a sample; a channel that provides a path through which the sample flows; and a valve that selectively opens and closes the channel with energy supplied from an outside; synchronizing and rotating a valve driver, which supplies the energy to the valve, and the microfluidic apparatus at a second rotation speed when the valve driver is aligned with the valve; and supplying the energy to the valve by using the valve driver to operate the valve.

The sample processing may include centrifuging the sample, and the second rotation speed may be lower than the first rotation speed.

While the sample processing is being performed, the valve driver may not be rotated.

The synchronizing and rotating the valve driver and the microfluidic apparatus may include: moving the valve driver in a radial direction of the microfluidic apparatus to align the valve driver with the valve in the radial direction; and aligning an angular position of the valve driver with an angular position of the valve.

The aligning the valve driver with the valve in the radial direction may be performed before rotating the valve driver.

The aligning the valve driver with the valve in the radial direction may be performed while the sample processing is being performed.

The aligning the valve driver with the valve in the radial direction may be performed simultaneously with the rotating of the valve driver.

According to another aspect of the present invention, a dynamic valve operation method includes: (a) rotating a microfluidic apparatus, the microfluidic apparatus including: a chamber that is a space accommodating a fluid; a channel that provides a path through which the fluid flows; and a valve that selectively opens and closes the channel with energy supplied from an outside; (b) synchronizing and rotating a valve driver, which supplies the energy to the valve, and the microfluidic apparatus at a second rotation speed when the valve driver is aligned with the valve; and (c) supplying the energy to the valve by using the valve driver to operate the valve.

Step (b) may include: moving the valve driver in a radial direction of the microfluidic apparatus to align the valve driver with the valve in the radial direction; and aligning an angular position of the valve driver with an angular position of the valve.

The aligning the valve driver with the valve in the radial direction may be performed before rotating the valve driver.

The aligning the valve driver with the valve in the radial direction may be performed simultaneously with the rotating of a valve driver.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
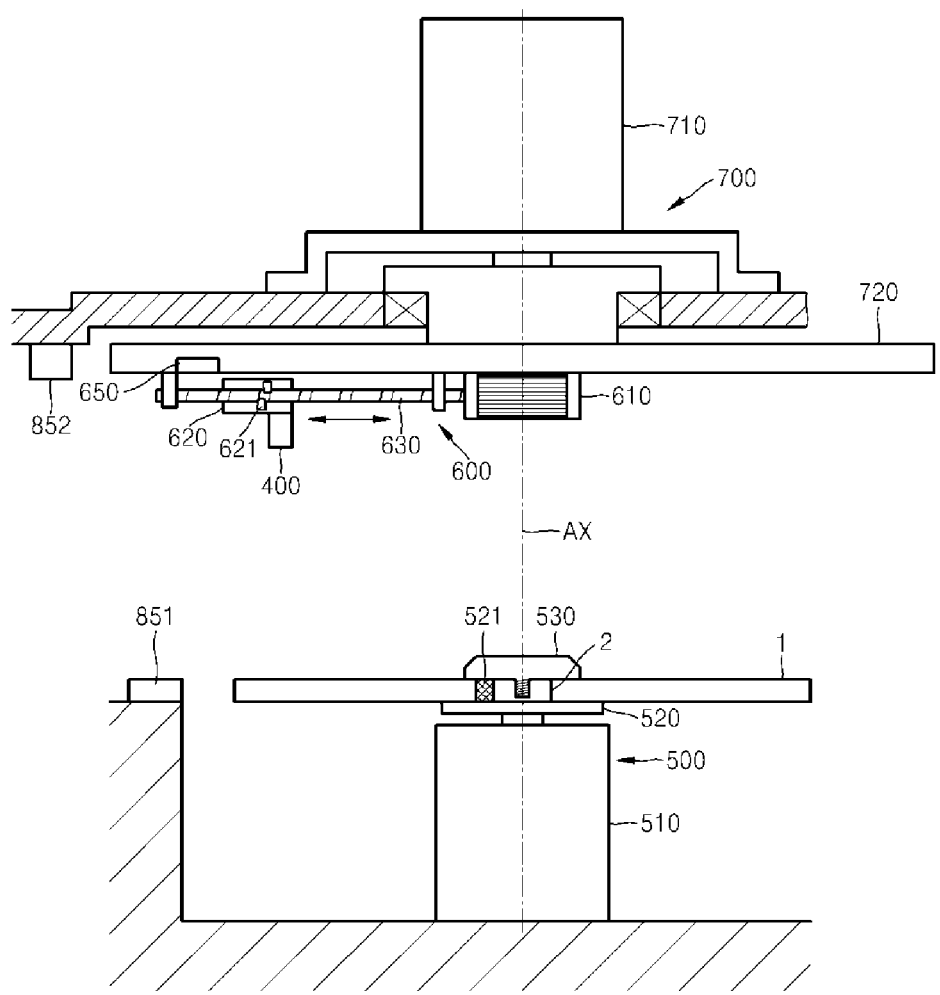
FIG. 1 is a diagram illustrating a schematic configuration of a sample analysis apparatus according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Figure 2:
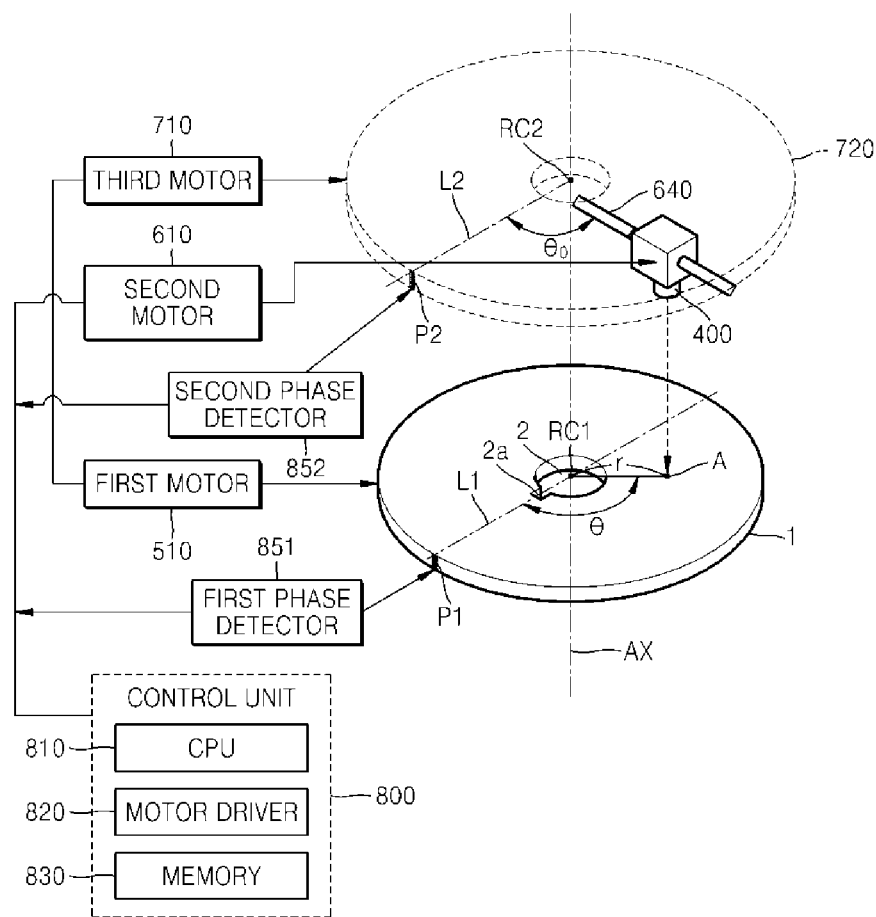
FIG. 2 is a block diagram illustrating an embodiment of the sample analysis apparatus of FIG. 1.

FIG. 1 is a diagram illustrating a schematic configuration of a sample analysis apparatus according to an embodiment of the present invention, and FIG. 2 is a block diagram illustrating an embodiment of the sample analysis apparatus of FIG. 1. Referring to FIGS. 1 and 2, a first unit 500 rotates a microfluidic apparatus 1 to generate a centrifugal force that is used to centrifuge and move a sample. For example, the first unit 500 includes a first motor 510. A turn table 520 with the microfluidic apparatus 1 mounted thereon is provided at a rotation axis of the first motor 510. A mounting part 2 corresponding to the turn table 520 is provided at the microfluidic apparatus 1. The mounting part 2 has the form of a through hole that passes through the center of the microfluidic apparatus 1 so as to enable the turn table 520 to be inserted thereinto, but the scope of the present embodiment is not limited thereto. When the microfluidic apparatus 1 is mounted on the turn table 520, a fixing cap 530 may be coupled to the turn table 520 from an upper portion of the microfluidic apparatus to fix the microfluidic apparatus 1 to the turn table 520. The fixing cap 520 may be fixed to the turn table 520 by various coupling types, for example, a screw coupling type, a clamping type, or a magnetic coupling type. In FIG. 1, the turn table 520 may be directly connected to the first motor 510. Alternatively, the first motor 510 may be connected to the turn table 520 by a power connection element such as a belt, a chain, a gear, or the like.

The electromagnetic wave generator 400 is an example of a valve driver that supplies energy to a valve A of the microfluidic apparatus 1 so as to drive the valve A. The electromagnetic wave generator 400 may irradiate valve A with an electromagnetic wave (for example, a laser beam). The electromagnetic wave generator 400 may be, for example, a laser diode.

A second unit 600 aligns the electromagnetic wave generator 400 with the valve A. That is, the second unit 600 moves the electromagnetic wave generator 400 in a radial direction of the microfluidic apparatus 1, and disposes the electromagnetic wave generator 400 above the valve A. In FIG. 1, an example of the second unit 600 is illustrated. The second unit 600 may include a second motor 610, a moving member 620 on which the electromagnetic wave generator 400 is mounted, and a lead screw 630 that is rotated by the second motor 610. The moving member 620 may be supported by a guide rail 640 that extends in the radial direction of the microfluidic apparatus 1. An engaging part 621, which is engaged with a spiral groove of the lead screw 630, is provided at the moving member 620. Due to such a configuration, when the lead screw 630 is rotated, the moving member 620 is moved in the radial direction along the guide rail 640. As an example of a method of obtaining a reference position in the radial direction of the electromagnetic wave generator 400, a method of using a change in a driving current of the second motor 610 may be used. For example, the moving member 620 is moved inward or outward in the radial direction by the second motor 610. When the moving member 620 is moved to an end of the lead screw 630, the moving member 610 is no longer moved, at which time an intensity of a current driving the second motor 610 is rapidly changed. When a rapid change in the current is sensed, the electromagnetic wave generator 400 may be recognized as being disposed at an inner end or an outer end in the radial direction, and a control unit 800 may recognize a corresponding position as the reference position in the radial direction of the electromagnetic wave generator 400. As another method, the second unit 600 may further include a position detector 650 that detects the reference position in the radial direction of the electromagnetic wave generator 400. The position detector 650 may detect the moving member 620 from, for example, an arbitrary position in the radial direction. The position detector 650 may be, for example, a non-contact sensor such as an optical sensor or a contact sensor such as a micro switch. An embodiment of the second unit 600 is not limited to an example illustrated in FIGS. 1 and 2. For example, the moving member 620 may be coupled to a belt or a wire which is circularly run in the radial direction.

The microfluidic apparatus 1 includes a microfluidic structure that includes a chamber accommodating a sample, a channel that provides a path for a flow of the sample, and the valve A that selectively opens and closes the channel. The microfluidic apparatus 1 may have, for example, a rotatable disk shape. The microfluidic apparatus 1 may include a lower structure in which an engraved microfluidic structure including a plurality of chambers forming an accommodating space for a fluid and a channel providing a path for the fluid between the chambers is formed, and an upper structure (an upper plate) that is coupled to the lower structure to form an upper wall of the microfluidic structure. The microfluidic apparatus 1 may have a double-plate structure in which the upper plate is coupled to a lower plate with the microfluidic structure disposed thereon. Also, the microfluidic apparatus 1 may have a triple-plate structure in which a partition plate defining the microfluidic structure is disposed between the upper plate and the lower plate. Plates may be bonded by an adhesive or a double-sided adhesive tape, or may be bonded by various methods such as ultrasound bonding, laser bonding, etc. The microfluidic apparatus 1 may be formed of a plastic material that is moldable and has a biologically inactive surface, and examples of such plastic material include acryl and PDMS. However, a material for the microfluidic apparatus 1 is not limited thereto, and may be any one of various materials that have chemical and biological stabilities, optical transparency, and mechanical processability.

Various kinds of valves A may be provided at the microfluidic apparatus 1. For example, examples of the valves A may include a normally closed valve that closes a channel in a normal state and opens the channel with energy supplied from the outside, a normally open valve that opens a channel in a normal state and closes the channel with energy supplied from the outside, and an open-close valve that is switchable to a channel-opened state, a channel-closed state, and a channel-opened state, sequentially.

Figure 3A:
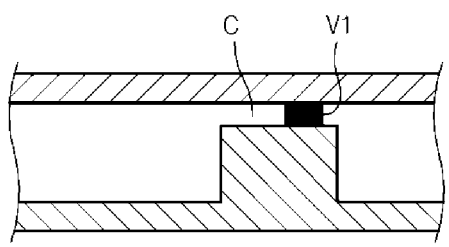
FIGS. 3A and 3B are cross-sectional views illustrating an embodiment of a normally closed valve.
Figure 3B:
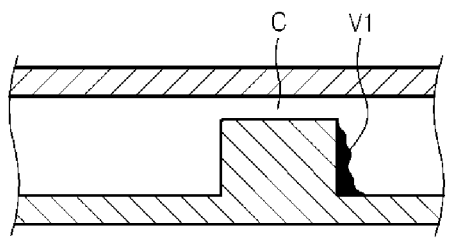

FIGS. 3A and 3B are cross-sectional views illustrating an embodiment of the normally closed valve. The normally closed valve may include a valve material V1 that is solid at a normal temperature. The valve material V1 is disposed as a solidified material at a channel C, and thus, as illustrated in FIG. 3A, the channel C is closed. The valve material V1 is melted with energy supplied from the outside, and moved to outside the channel C by a centrifugal force, and as illustrated in FIG. 3B, the valve material V1 is again solidified with the channel C being open.

Figure 4A:
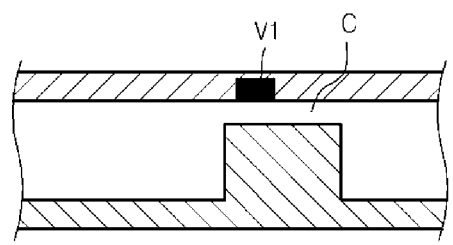
FIGS. 4A to 4C are cross-sectional views illustrating an embodiment of a normally open valve and an open-close valve.
Figure 4B:
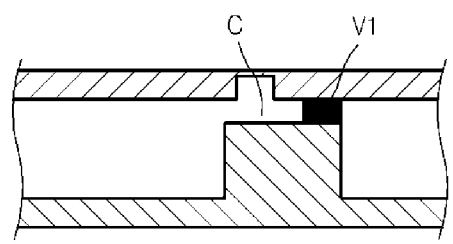
Figure 4C:
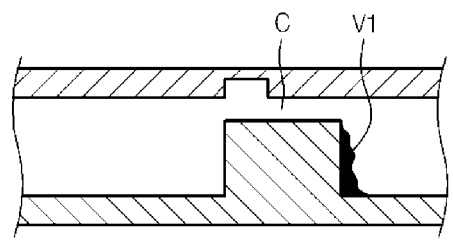

FIGS. 4A to 4C are cross-sectional views illustrating an embodiment of the normally open valve and the open-close valve. The normally open valve may include the valve material V1 that is solid at the normal temperature. The valve material V1 is disposed as a solidified material on the channel C, and thus, as illustrated in FIG. 4A, the channel C is maintained in an open state. The valve material V1 is melted with energy supplied from the outside. The valve material V1 having increased fluidity is moved into the channel C, and after a certain time elapses, the valve material V1 is solidified in the channel C. Therefore, as illustrated in FIG. 4B, the channel C is closed. An amount of energy to be applied may be determined depending on a kind of the valve material V1, and for example, may be determined such that the valve material V1 is melted and moved by the centrifugal force. For example, an amount of energy needed to melt the valve material V1 may be from about 1 mW to about 5 W.

The open-close valve may be implemented by processes illustrated in FIGS. 4A to 4C. When external energy is supplied to the valve material V1 in a state illustrated in FIG. 4B, the state is switched to a state illustrated in FIG. 4C. Such a process is as described above with reference to FIGS. 3A and 3B.

Externally irradiated energy may include, for example, an electromagnetic wave, and an energy source may include a laser source, which emits a laser beam, or a light emitting diode or a xenon lamp which emits visible light or infrared light. When the energy source is the laser source, the energy source may include at least one laser diode. The energy source may be selected depending on a wavelength of an electromagnetic wave which is capable of being absorbed by exothermic particles included in the valve material V1. As a valve material V1, a thermoplastic resin, such as a cyclic olefin copolymer (COC), polymethylmethacrylate (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF) may be used. In addition, as the valve material V1, a phase change material that exists in a solid state at room temperature may be used. The phase change material may include wax. When heated, wax dissolves into a liquid state and a volume thereof expands. Examples of the wax are paraffin wax, microcrystalline wax, synthetic wax, and natural wax. The phase change material may include a gel or a thermoplastic resin. As the gel, polyacrylamide, polyacrylates, polymethacrylates, or polyvinylamides may be used. A plurality of fine exothermic particles that absorb electromagnetic wave energy and emits heat, may be dispersed in the valve material V1. Fine exothermic particles may have an average particle size of from about 1 nm to about 100 μm to freely pass the fine channel C having a depth of about 0.1 mm and a width of about 1 mm. Fine exothermic particles may have an exothermic property, and thus, when electromagnetic wave energy is supplied by, for example, exposure to laser light, a temperature thereof increases rapidly, and the fine exothermic particles may homogeneously disperse in wax. To obtain such a property, each of the fine exothermic particles may have a core including a metallic component and a hydrophobic surface structure. For example, the fine exothermic particles may each have a molecular structure in which a plurality of surfactants are bound to and cover a Fe-core. The fine exothermic particles may be preserved in a dispersion state in carrier oil. The carrier oil may also be hydrophobic to allow the fine exothermic particles having a hydrophobic surface structure to be homogeneously dispersed. Carrier oil with the fine exothermic particles dispersed therein is mixed with a molten phase change material, and the mixture is loaded into the channel C and solidified to clog the channel C. The fine exothermic particles are not limited to the polymer particles presented as an example of the fine exothermic particles, and quantum dots or magnetic beads may also be used as fine exothermic particles. In addition, the fine exothermic particles may include, for example, a fine metal oxide, such as $Al_2O_3$, $TiO_2$, $Ta_2O_3$, $Fe_2O_3$, $Fe_3O_4$, or, $HfO_2$. In addition, no fine exothermic particles may be necessarily included in the normally closed valve, and according to another embodiment of the present invention, the normally closed valve may be a phase change material without any fine exothermic particles.

The channel C may be opened by the electromagnetic wave generator 400 so as to allow for a sample to move between the chambers of the microfluidic apparatus 1. To this end, rotation of the microfluidic apparatus 1 is stopped, the second unit 600 moves the electromagnetic wave generator 400 to a position facing the valve A, and the valve material V1 is melted by irradiating valve material V1 with an electromagnetic wave (for example, a laser beam). Then, the first unit 500 rotates the microfluidic apparatus 1, and thus, the melted valve material V1 is moved to inside or outside the channel C by a centrifugal force. The valve material V1 is again solidified inside or outside the channel C, and thus, the channel C is opened or closed. However, much time (a restart time or restart period) is needed to rotate the microfluidic apparatus 1 to generate the centrifugal force capable of moving the melted valve material V1 after the valve material V1 is melted. Moreover, the valve material V1 may be cooled during the restart period, and thus a fluidity of the valve material V1 may be degraded. The fluidity-degraded valve material V1 may not sufficiently be moved to inside or outside the channel C, and thus, the channel C may be insufficiently closed or opened. Furthermore, the valve A may not operate when the valve material V1 is partially or wholly solidified during the restart period.

Moreover, when the valve A operates after a sample is centrifuged in the microfluidic apparatus 1, it is required to perform a process that stops the microfluidic apparatus 1, moves the electromagnetic wave generator 400 to a position facing the valve A, melts the valve material V1 using an electromagnetic wave, and again rotates the microfluidic apparatus 1. Since the centrifugal force is not applied to the centrifuged sample while the process is being performed, centrifuged layers may be mixed with each other, and the mixing of the centrifuged layers may result in a less reliable sample analysis.

To solve the above-described problems, the sample analysis apparatus has a dynamic valve operation structure that operates the valve A while the microfluidic apparatus 1 is rotating. Referring to FIGS. 1 and 2, the sample analysis apparatus further includes a third unit 700 that rotates the electromagnetic wave generator 400. The third unit 700 rotates the electromagnetic wave generator 400 with respect to a rotation center RC2 forming the same axis with a rotation center RC1 of the microfluidic apparatus 1. That is, the rotation centers RC1 and RC2 are disposed on a common rotation axis AX. The third unit 700 rotates the electromagnetic wave generator 400 in synchronization with rotation of the microfluidic apparatus 1. As an example, the third unit 700 may include a third motor 710 and a rotary member 720 that is rotated by the third motor 710. The second unit 600 may be disposed on the rotary member 720. For example, the second motor 610, the guide rail 640, and the lead screw 630 may be disposed on the rotary member 720. In FIG. 1, the third motor 710 may be directly connected to the rotary member 720, but the third motor 710 may be connected to the rotary member 720 by a power connection element such as a belt, a chain, a gear, or the like.

The control unit 800 controls the first to third motors 510, 610 and 710, and overall controls a sample analysis process. The control unit 800 may include a memory 830, a motor driver 820 that drives the first to third motors 510, 610 and 710, and a central processing unit (CPU) 810. Application software for controlling the sample analysis process may be stored in the memory 830. Also, the memory 830 may store position coordinate values (for example, a polar coordinate value (r, θ) with respect to the rotation center RC1 and a first reference line L1) of the plurality of valves A included in the microfluidic apparatus 1. The application software and the position coordinate values of the plurality of valves A may be downloaded from a host computer, and stored in the memory 830. Also, a user may directly input the position coordinate values of the plurality of valves A to the memory 830 using an input unit (not shown).

The first motor 510 may be a servomotor. An encoder for counting the number of rotations and a feedback mechanism for controlling rotation are built into the servomotor. Therefore, a rotation phase of the first motor 510, for example, an angular position of the reference position of the encoder with respect to a control reference polar coordinate system of the sample analysis apparatus may be obtained at an arbitrary time. When the microfluidic apparatus 1 is mounted on the first motor 510, the reference position of the encoder of the first motor 510 is aligned with the first reference line L1 of the microfluidic apparatus 1. Therefore, an angular position of the valve A for the control reference polar coordinate system of the sample analysis apparatus may be obtained at an arbitrary time. For example, a first alignment part (2a of FIG. 2) aligned with the first reference line L1 may be provided on the mounting part 2 of the microfluidic apparatus 1, and a second alignment part (521 of FIG. 1) which is coupled to the first alignment part 2a and aligned with the reference position of the encoder of the first motor 510 may be provided on the turn table 520. The first and second alignment parts 2a and 521 may have a complementary shape. For example, the first alignment part 2a may have the form of a groove extending from the circle-shaped mount part 2 to an outer side, and the second alignment part 521 may have the form of a projection inserted into the first alignment part 2a.

The third motor 710 may be a servomotor. A second reference line L2 of the rotary member 720 may be aligned with the reference position of the encoder built into the third motor 710. The second reference line L2 may match a moving trace in the radial direction of the electromagnetic wave generator 400. Also, as illustrated in FIG. 2, the second reference line L2 may have a phase difference "$\theta_0$" with the moving trace in the radial direction of the electromagnetic wave generator 400.

As another example, referring to FIGS. 1 and 2, the sample analysis apparatus may further include first and second phase detectors 851 and 852. For example, the first phase detector 851 may detect a first phase pattern P1 provided on the microfluidic apparatus 1, and the second phase detector 852 may detect a second phase pattern P2 provided on the rotary member 720. The first phase pattern P1 is provided at a position aligned with the first reference line L1 of the microfluidic apparatus 1, and the second phase pattern P2 is provided at a position aligned with the second reference line L2 of the rotary member 720. The control unit 800 may calculate the number of rotations of the microfluidic apparatus 1 and an angular position of the first reference line L1 on the basis of an output signal (a first phase signal) of the first phase detector 851, the number of rotations of the rotary member 720 and an angular position of the second reference line L2 on the basis of an output signal (a second phase signal) of the second phase detector 852, and an angular position of each of the valve A and the electromagnetic wave generator 400 at an arbitrary time. Each of the first and second phase patterns P1 and P2 may be, for example, an optically detectable pattern or a magnetically detectable pattern. The phase pattern P1 may be a position marker aligned with the first alignment part 2a. When the first and second phase detectors 851 and 852 are provided, each of the first and third motors 510 and 710 may not be a servomotor including an encoder.

Hereinafter, a process of dynamically closing/opening the valve having the above-described configuration, for example, a process of opening the valve A illustrated in FIGS. 3A and 3B, will be described in detail.

[Sample Processing]

The control unit 800 performs a sample processing process including centrifuging a sample, mixing the sample with additives, etc. according to an analysis purpose by rotating the microfluidic apparatus 1 using the first unit 500. For example, a sample is loaded into the microfluidic apparatus 1, and by rotating the microfluidic apparatus 1, the sample is centrifuged. Then, depending on the case, the valve A is opened for transferring some or all of a plurality of centrifuged material layers to another chamber. While [Sample Processing] is being performed, the rotary member 720 may be maintained in a stop state without rotating.

[Position Alignment in Radial direction]

The control unit 800 drives the second unit 600 to align the electromagnetic wave generator 400 with the valve A, e.g., a radial position of the electromagnetic wave generator 400 with a radial position of the valve A. To this end, the control unit 800 reads out coordinates, r, in the radial direction of the valve A from the memory 830. The control unit 800 may detect a rapid change in an intensity of a current used to drive the second motor 610 while driving the second motor 610, and recognize a change-detected position as a reference position $r_0$ in the radial direction of the electromagnetic wave generator 800. As another example, the control unit 800 drives the second motor 610 to move the moving member 620 in the radial direction, and detects the moving member 620 by using the position detector 650. If the moving member 620 is detected, the control unit 800 recognizes the electromagnetic wave generator 400 as being disposed at the reference position $r_0$ in the radial direction. The control unit 800 determines the number of rotations and a rotation direction of the second motor 610 corresponding to a value of "$r-r_0$", and moves the electromagnetic wave generator 400 in the radial direction on the basis of the determined number of rotations and the determined rotation direction. [Position Alignment in the Radial Direction] may be previously performed (and recorded) in a state where the rotary member 720 is stopped without rotating while [Sample Processing] is being performed.

[Angular Position Alignment]

Subsequently, the control unit 800 drives the third unit 700 to rotate the electromagnetic wave generator 400 in synchronization with the microfluidic apparatus 1. The control unit 800 reads out the angular position θ of the valve A from the memory 830. The control unit 800 drives the third motor 710 using the motor driver 820. The control unit 800 controls the third motor 710 to match a rotation speed of the rotary member 720 with a rotation speed of the microfluidic apparatus 1, on the basis of an encoder output signal (a first encoder output signal) of the third motor 710 or an output signal (a second phase signal) of the second phase detector 852. Subsequently, the control unit 800 calculates angular positions of the electromagnetic wave generator 400 and the valve A, respectively, with respect to the reference polar coordinate systems based on encoder output signals (first and second encoder output signals) of the first and third motors 510 and 710 or output signals (first and second phase signals) of the first and second phase detectors 851 and 852 at an arbitrary time, and determines a difference between the calculated angular positions. The control unit 800 provides feedback control of the number of rotations of the third motor 710 on the basis of the difference, thereby matching the angular positions of the electromagnetic wave generator 400 and the valve A with respect to the reference polar coordinate systems with each other. Therefore, the electromagnetic wave generator 400 is rotated in synchronization with the microfluidic apparatus 1.

Figure 5:
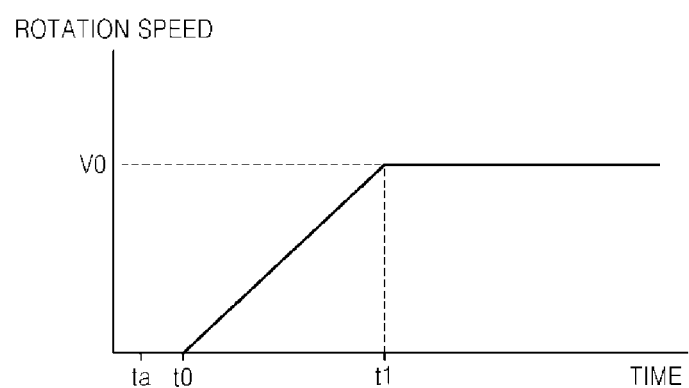
FIG. 5 is a graph showing an embodiment of a method of driving a third motor.

As another example, as illustrated in FIG. 5, when the rotation speed of the microfluidic apparatus 1 is V0, the control unit 800 may determine a starting time of the third motor 710 such that the electromagnetic wave generator 400 is disposed above or proximal the valve A of the microfluidic apparatus 1 at a time t1 when the rotary member 720 reaches the rotation speed V0 from a stop state (t=t0), namely, the angular positions of the electromagnetic wave generator 400 and the valve A are aligned. "t1−t0" may be determined according to a driving method of the third motor 710, and an angular position with respect to the reference polar coordinate system of the valve A at the time t1 may be obtained from the encoder output signal of the first motor 510 or the output signal of the first phase detector 851. Therefore, a delay time "t0−ta" may be determined such that the angular positions of the electromagnetic wave generator 400 and the valve A are aligned at the time t1, on the basis of the angular position θ of the valve A read out from the memory 830 at a time to when the first reference line L1 is aligned with the second reference line L2.

A rotation speed (a second rotation speed) of the microfluidic apparatus 1 in [Angular Position Alignment] may differ from a rotation speed (a first rotation speed) in [Sample Processing]. For example, the rotation speed (the first rotation speed) for centrifuging a sample may be very fast, and thus, in the angular position alignment process, the microfluidic apparatus 1 may be rotated at the second speed slower than the first rotation speed. For example, the second rotation speed may be adjusted so as to generate a centrifugal force that does not allow material layers to be mixed with each other while [Angular Position Alignment] is performed, in consideration of parameters including an amount of a sample and a mass and a viscosity of materials forming the sample.

[Valve Operation]

When the electromagnetic wave generator 400 is rotated in synchronization with the microfluidic apparatus 1 by performing [Position Alignment in the Radial Direction] and [Angular Position Alignment], the control unit 800 drives the electromagnetic wave generator 400 to irradiate, for example, a laser beam onto the valve material V1. Therefore, energy of the laser beam is absorbed into or by the valve material V1, thereby melting the valve material V1. Since the microfluidic apparatus 1 is being rotated, as illustrated in FIG. 3B, the melted valve material V1 is pushed to outside the channel C by the centrifugal force, and thus, the valve A is opened.

As described above, the valve A is driven while the electromagnetic wave generator 400 is being rotated in synchronization with the microfluidic apparatus 1, and thus, the channel C is opened or closed by the centrifugal force before the melted valve material V1 is solidified, thereby enhancing an operation reliability and speed of the valve A. Also, since the microfluidic apparatus 1 is continuously rotated while the valve A is being driven, the centrifuged sample is maintained in a centrifuged state, thereby preventing centrifuged layers from being mixed with each other. Also, an operation of driving the valve A is performed without a rotation stop operation of the microfluidic apparatus 1, and thus, a time taken to perform sample analysis is shortened.

Figure 6:
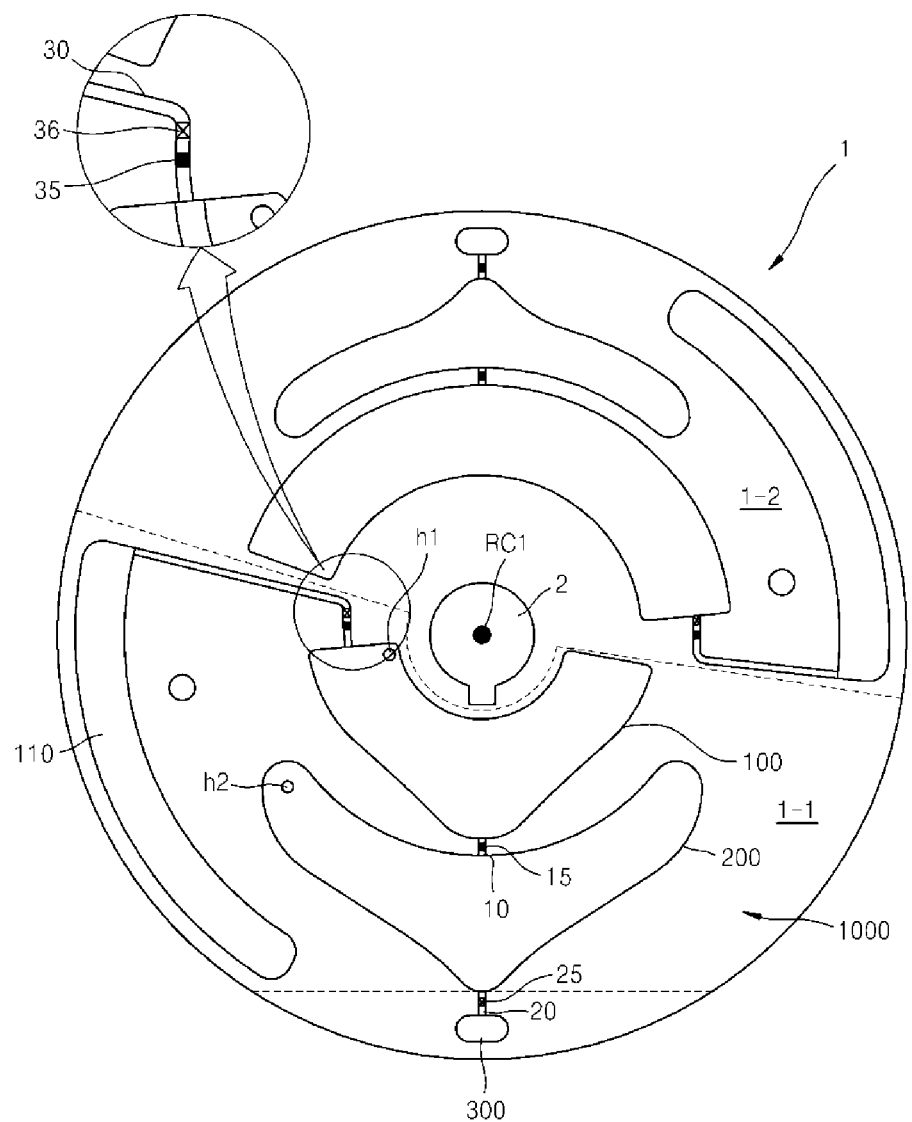
FIG. 6 is a configuration diagram illustrating an embodiment of a microfluidic apparatus.

FIG. 6 is a configuration diagram illustrating an embodiment of the microfluidic apparatus 1. The microfluidic apparatus 1 may have a single microfluidic structure or a plurality of microfluidic structures. For example, the microfluidic apparatus 1 may be divided into a few regions, each of which may include a microfluidic structure that operates independently. For example, the microfluidic apparatus 1 according to the present embodiment includes two regions 1-1 and 1-2, each including a microfluidic structure. The microfluidic structures of the regions 1-1 and 1-2 may have substantially identical structures, and thus, hereinafter, only the microfluidic apparatus 1 of the region 1-1 is described in detail.

A separation unit 1000, which separates a target cell from a biological sample using a centrifugal force, is provided outside the radial direction with respect to the rotation center RC1 of the microfluidic apparatus 1. A collection chamber 300, which collects target cells, is provided outside the separation unit 1000 in the radial direction. The separation unit 1000 may include a sample chamber 100 and a separation chamber 200 that are connected to each other by a sample channel 10. The separation chamber 200 is connected to the collection chamber 300 by a collection channel 20. A sample valve 15 and a collection valve 25, which control a flow of a fluid, are respectively disposed on or within the sample channel 10 and the collection channel 20.

The sample chamber 100 provides a sample including a target cell-fine bead complex, namely, a target material. A target cell contained in the sample and fine beads contact each other in the sample chamber 100, and the fine beads are bonded to the target cell, thereby forming the target cell-fine bead complex. The fine beads may be, for example, solid microbeads, magnetic beads, gel beads, or polymer microbeads. As an example, an inlet hole h1 for loading a sample may be provided at the sample chamber 100. The fine beads may be loaded into the sample chamber 100 through the inlet hole h1 before a target cell separation process is performed. The inlet hole h1 may be provided in the upper plate (not shown). When the microfluidic apparatus 1 is manufactured for a predetermined task, fine beads suitable for the task may be introduced in the sample chamber 100 during the procedure of manufacturing the microfluidic apparatus 1.

The target cell may include a circulating tumor cell (CTC), a cancer stem cell, or a cancer cell. For example, the target cell may include a cell in a cancer or tumor selected from the group comprising bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, adult T-cell leukemia, lymphoma, multiple myeloma, glioblastoma/astrocytoma, melanoma, mesothelioma, and Wilms' tumor, but is not limited thereto.

The sample may include any of a number of biological samples as long as the target cell exists therein. For example, the biological sample may be selected from the group comprising a biopsy sample, a tissue sample, a cell suspension having a separated cell suspended in a liquid medium, a cell culture, and any combinations thereof, but may not be limited thereto. The sample may also be selected from the group comprising blood, marrow fluid, saliva, lacrimal fluid, urine, semen, mucous fluid, and any combinations thereof, but is not limited thereto. For example, in order to separate CTCs, blood may be used as the sample.

At least one ligand specific to a surface marker of a target cell is bound to the fine beads. The fine beads serve to increase the density of the target cell by binding to the target cell. The fine beads may have a density value which may cause a density difference between the target cell and another cell in the sample. For example, when the biological sample is blood containing a cancer cell as the target cell, and since white blood cells (WBCs) and red blood cells (RBCs) have densities of about 1.07 $g/cm^3$ and about 1.1 $g/cm^3$, respectively, fine beads with an appropriate density may be selected in consideration of such densities. For example, the fine particles may be selected from the group comprising polystyrene particles, polymethylmethacrylate particles, latex particles, acrylonitril-butadiene-styrene copolymer (ABS) particles, and a complex thereof, but is not limited thereto. A diameter of the fine beads may vary according to the type of the target cell to be separated and the type of beads to be used. The diameter may be, for example, from about 1 nm to about 100 μm, or from about 10 nm to about 10 μm.

The surface marker may include a marker selected from the group comprising protein, sugar, lipid, nucleic acid, and any combinations thereof, but is not limited thereto. For example, the surface marker may be a protein, e.g., an antigen, which is specifically expressed in a cancer or tumor cell and is displayed in a cell membrane, such as epithelial cell adhesion molecule (EpCAM), c-Met, cytokeratines, CD45, Human Epidermal Growth Factor Receptor 2 (Her2), or any combinations thereof. In addition, the at least one ligand specific to the surface marker may be an antibody which may bind specifically to an antigenic protein.

In the separation chamber 200, a target material is separated from a sample supplied from the sample chamber 100. A density gradient medium (DGM) is accommodated in the separation chamber 200. The DGM is used to separate a target material from a sample using a density gradient. A density of the DGM is lower than that of a target material, and is greater than a fluid other than the target material. Therefore, upon centrifugation, the DGM may be located between the fluid and the target material, and may separate the target material from the fluid within the separation chamber 200. An inlet hole h2 for loading the DGM may be provided at the separation chamber 200. The inlet hole h2 may be provided in the upper plate (not shown). When the microfluidic apparatus 1 is to be used for a particular task, the DGM suitable for the task can be introduced in the separation chamber 200 in advance, for example, during the procedure of manufacturing the microfluidic apparatus 1.

In order for a sample to flow from the sample chamber 100 to the separation chamber 200 due to a centrifugal force, the separation chamber 200 is disposed outside the sample chamber 100 in the radial direction with respect to the rotation center RC1. In the separation chamber 200, the target material and the fluid are separated from each other with the DGM therebetween. The target material is collected at the lowermost layer of the separation chamber 200, namely, at the outermost side in the radial direction with respect to the rotation center RC.

The collection chamber 300 is disposed outside the separation chamber 200 in the radial direction with respect to the rotation center RC1. The collection chamber 300 is connected to the separation chamber 200 by the collection channel 20. In the separation chamber 200, the target material is collected at the lowermost layer of the separation chamber 200, and when the collection channel 20 is opened by the collection valve 25, the target material flows into the collection chamber 300 due to the centrifugal force.

As illustrated in FIG. 2, the separation unit 1000 may further include a waste chamber 110. The waste chamber 110 is disposed outside the sample chamber 100 in the radial direction with respect to the rotation center RC1. The waste chamber 110 is connected to the sample chamber 100 by a discharge channel 30. Discharge valves 35 and 36 for controlling a flow of the fluid may be provided on or within the discharge channel 35.

A portion of a sample in the sample chamber may be removed before the target material is formed in the sample chamber 100. For example, the sample may be centrifuged in the sample chamber 100, and an upper material layer disposed at an upper portion of a target cell may be discharged into the waste chamber 110. Then, the target cell may be bonded to fine beads by mixing the fine beads and the sample, thereby forming the target material. For example, when blood including a CTC is centrifuged in the sample chamber 100, a plasma layer is located at the uppermost layer which is closest to the rotation center RC1 in the sample chamber 100, and may be discharged into the waste chamber 110. Protein included in the plasma layer is bonded to the fine beads, causing a bonding rate of the CTC and the fine beads. Therefore, by removing the plasma layer, the bonding rate of the CTC and the fine beads is enhanced.

A microfluidic valve may be applied as each of the valves 15, 25, 35 and 36. Each of the valves 15 and 35 may be a normally closed valve that closes the channels 10 and 30 in a normal state and opens the channels 10 and 30 with energy supplied from the outside, and each of the valves 25 and 36 may be a normally open valve that opens the channels 20 and 30 in a normal state and closes the channels 20 and 30 with energy supplied from the outside.

Hereinafter, an embodiment of the above-described microfluidic apparatus 1 and an example of a process of enriching and separating a target cell using an embodiment of the sample analysis apparatus of FIGS. 1 and 2 will be described. In the present embodiment, blood including a CTC is used as a sample.

[Preparation]

About 5 mL of a blood containing CTCs as a target cell and more than about $1 \times 10^8$ of fine beads combined with an antibody that binds specifically to an antigen on the target cell are loaded into the sample chamber 100 through the inlet hole h1. In addition, an appropriately selected DGM is loaded into the separation chamber 200 through the inlet hole h2. For example, the DGM may be Ficoll, Percoll, polysaccharide, or sodium chloride (NaCl) solution. WBCs and CTCs having similar physical properties are isolated in an identical layer upon density gradient centrifugation. Thus, in the present embodiment, only CTCs are separated from the blood by binding the fine beads to the CTCs to induce a density difference from the WBCs. For example, the fine beads may be melamine particles having a density of about 1.57 g/cm$^3$, which is greater than a density of about 1.05 to about 1.1 g/cm$^3$ of biological particles present in the blood.

[Blood Centrifugation]

As described above, the specific binding of the fine beads and the target cell may depend on an antigen-antibody binding affinity. A sample may contain various kinds of proteins and such proteins may prohibit the specific binding between the fine beads and the target cell. For example, binding between the fine beads and the target cell may be prevented when a protein that has a structure similar to an antigen is bound to a surface marker of the target cell in advance. In addition, binding between the fine beads and the target cell may be prevented when a protein that has a structure similar to an antibody is bound to a ligand of the fine beads. As such, proteins in the sample prevent generation of a target cell-fine beads complex, thereby lowering enrichment efficiency of the target cell. To prevent the decrease in the enrichment efficiency, proteins in the sample may be removed from the sample before the fine beads are mixed with the sample.

In this regard, after the blood containing the circulating cancer cells as a target cell is loaded into the sample chamber 100, the microfluidic apparatus 1 is mounted on the turn table 520 and is rotated for about five minutes at a rate of about 1000 to about 8000 rpm, e.g., about 3000 rpm. Then, in the sample chamber 100, the blood is separated into a plurality of layers according to density differences. An RBC layer containing RBCs that are heaviest is located at an outermost portion of the sample chamber 100 in the radial direction. A target layer containing WBCs and the target cell, and a plasma layer as an upper material layer are sequentially arranged next to the RBC layer. Since proteins in the blood excluding blood cells are lighter than the blood cells, the proteins are disposed in the plasma layer.

[Plasma Discharge]

While the microfluidic apparatus 1 is being rotated at the rotation speed (the first rotation speed) in centrifugation or at the rotation speed (the second rotation speed) lower than the first rotation speed, the discharge valve 35 is opened. For example, the electromagnetic wave generator 400 may irradiate a laser beam onto the discharge valve 35, while the electromagnetic wave generator 400 is being rotated in synchronization with the microfluidic apparatus 1 by performing [Position Alignment in the Radial Direction] and [Angular Position Alignment] on the basis of the polar coordinate value of the discharge valve 35 which is read out from the memory 830. Since the discharge valve 35 is opened while the electromagnetic wave generator 400 is being rotated, centrifuged layers (a RBC layer, a target layer, and a plasma layer) in the sample chamber 100 are not disturbed because a centrifugal force is continuously applied thereto.

By rotating the microfluidic apparatus 1 at the second rotation speed or at a different rotation speed (a rotation speed for discharging plasma), the plasma is discharged into the waste chamber 110 through the discharge channel 30 by the centrifugal force. In this process, all or some of the proteins in blood which prohibit bonding of a target cell and fine beads are discharged into the waste chamber 110 along with the plasma. Also, since the microfluidic apparatus 1 is being rotated at the second rotation speed, rapid acceleration is not needed even when increasing the rotation speed of the microfluidic apparatus 1 so as to discharge the plasma. Therefore, a risk of disturbing the centrifuged layers due to the rapid acceleration is reduced.

Subsequently, the electromagnetic wave generator 400 irradiates an electromagnetic wave (for example, a laser beam) onto the valve 36, thereby closing the discharge channel 30. This process may be performed when the microfluidic apparatus 1 is stopped. Also, as described above, the electromagnetic wave generator 400 irradiates the laser beam onto the valve 36 while the microfluidic apparatus 1 and the electromagnetic wave generator 400 are being rotated in synchronization with each other by performing [Position Alignment in the Radial Direction] and [Angular Position Alignment] on the basis of the polar coordinate value (which is read out from the memory 830) of the valve 36. Therefore, the valve material V1 is melted when a centrifugal force is being applied thereto, and thus, the melted valve material V1 may be moved into the valve 30 to close the channel 30. Accordingly, an operation error of the valve 36 is reduced.

[Target Material (Target Cell-Fine Beads Complex) Production]

The microfluidic apparatus 1 is repeatedly rotated clockwise and counterclockwise for a predetermined time so that the fine beads contact and are bound to the target cell, thereby forming a target material in the sample chamber 100.

[Fluid Transfer]

The electromagnetic wave generator 400 irradiates electromagnetic waves such as laser beams to the sample valve 15 to open the sample channel 10. Then, the valve material V1 melts and thus the sample channel 10 is opened. A process, which operates the sample valve 15 to open the sample channel 10, may be performed when the microfluidic apparatus 1 is stopped. Also, the electromagnetic wave generator 400 may irradiate the laser beam onto the sample valve 36 while the microfluidic apparatus 1 and the electromagnetic wave generator 400 are being rotated in synchronization with each other by performing [Position Alignment in the Radial Direction] and [Angular Position Alignment] on the basis of the polar coordinate value of the sample valve 15 which is read out from the memory 830. As described above, since the valve material V1 is melted while the centrifugal force is being applied thereto, the melted valve material V1 is easily removed from the sample channel 10, thereby opening the sample channel 10. Accordingly, an operation error of the sample valve 15 is reduced.

According to a centrifugal force generated by rotating the microfluidic apparatus 1, the fluid in the sample chamber 100 is transported to the separation chamber 200 that accommodates the DGM through the sample channel 10.

[Target Material Separation Using Density Gradient in Separation Chamber 200]

The microfluidic apparatus 1 is rotated for about 10 minutes at a rate of, for example, 4000 rpm. Then, in the separation chamber 200, the sample is separated into a plurality of layers according to density gradients of materials in the sample. For example, the sample may be divided into a DGM layer, an RBC layer, a WBC layer, and a plasma layer in the separation chamber 200. Since the target material containing the target cell bonded to the fine beads has the highest density, the target cell is separated from the WBC layer in the form of the target material and is located at a lowermost portion of the separation chamber 200, i.e., an outermost portion in the radial direction based on the rotation center RC1. Then, the DGM layer, the RBC layer, the WBC layer, and the plasma layer are sequentially arranged toward the rotational center RC1.

[Target Material Collection]

Since the collection valve 25 is opened, the target material located in the lowermost portion of the separation chamber 200 along with the DGM is transported to the collection chamber 300 through the collection channel 20. After the target material is transported, energy is supplied to the collection valve 25 to close the collection channel 20. A process of closing the collection valve 25 may be performed when the microfluidic apparatus 1 is stopped or while the microfluidic apparatus 1 is synchronized with the electromagnetic wave generator 400 as described above.

Subsequently, the target material collected in the collection chamber 300 is recovered using a pipette or the like through a discharge hole (not shown). Since the density and volume of the target material are greater than those of other cells in the blood, it is easy to separate the target material through filtration. Thus, upon subsequent filtration, an enriched target material excluding the fluid may be obtained.

The above-described sample analysis apparatus and method may be applied to the microfluidic apparatus 1 having various structures for various analyses such as blood chemistry analysis, immune examination, cell separation, etc.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A sample analysis apparatus comprising:
   a first unit that rotates a microfluidic apparatus comprising
      a chamber with a space for accommodating a sample;
      a channel that provides a path through which the sample flows;
   and a valve that selectively opens and closes the channel;
   a valve driver that supplies energy, used to operate the valve, to the valve in a state of being separated from the microfluidic apparatus;
   a second unit configured to move the valve driver in a radial direction of the microfluidic apparatus;
   a third unit configured to rotate the valve driver with respect to a common rotation axis with a rotation axis of the microfluidic apparatus, the third unit comprising:
   a rotary member that is rotatable with respect to the common rotation axis, and
   on which the valve driver is provided so as to be configured to move in the radial direction by the second unit and a motor that rotates the rotary member; and
   a control unit configured to control the first and third units and the valve driver to supply energy to the valve while the microfluidic apparatus and the valve driver are being rotated at the same rotation speed, wherein the control unit is configured to control the first, second, and third units so that positions in the radial direction and angular positions of the valve driver and the valve are aligned with each other.

2. The sample analysis apparatus of claim 1, further comprising a position detector configured to detect a reference position of the valve driver in the radial direction.

3. The sample analysis apparatus of claim 1, further comprising:
   a first phase detector configured to detect a first phase pattern provided on the microfluidic apparatus; and
   a second phase detector configured to detect a second phase pattern provided on the valve driver, wherein the control unit is configured to control angular positions of the valve and the valve driver, based on output signals of the first and second phase detectors.

4. The sample analysis apparatus of claim 1, wherein,
while a sample processing process is being performed, the control unit controls the first unit to rotate the microfluidic apparatus at a first rotation speed, and
while the valve is operating, the control unit controls the first and third units to rotate the microfluidic apparatus and the valve driver at a second rotation speed.

5. The sample analysis apparatus of claim 4, wherein the first rotation speed is the same as the second rotation speed.

6. The sample analysis apparatus of claim 4, wherein the first rotation speed differs from the second rotation speed.

7. The sample analysis apparatus of claim 6, wherein the second rotation speed is lower than the first rotation speed.

8. The sample analysis apparatus of claim 1, wherein the valve includes a valve material that is melted by energy supplied from the valve driver.

9. The sample analysis apparatus of claim 8, wherein the valve material is melted, and the melted valve material is discharged or moved through the channel by a centrifugal force generated by the rotation of the microfluidic apparatus so as to open or close the channel.

* * * * *